United States Patent
Soto et al.

[19]

[11] Patent Number: 6,014,029
[45] Date of Patent: Jan. 11, 2000

[54] SENSOR FOR SENSING CHANGES IN THE PERMITTIVITY OF A MEDIUM IN WHICH IT IS DISPOSED

[75] Inventors: Jaime J. Soto; Rolando A. Carmona; Andres Susaeta; Leonardo C. Herrera; Marcelo I. Lepe; Marcelo H. Orellana, all of Santiago, Chile

[73] Assignee: Climonics Ltda, Santiago, Chile

[21] Appl. No.: 08/968,635

[22] Filed: Nov. 12, 1997

[51] Int. Cl.[7] .......................... G01R 27/26; G01N 27/22
[52] U.S. Cl. .......................... 324/664; 324/667; 324/690; 137/78.3
[58] Field of Search .................................... 324/663, 664, 324/667, 668, 674, 675, 681, 682, 686, 689, 690, 71.1; 340/602, 604; 73/29.01, 335.04

[56] References Cited

U.S. PATENT DOCUMENTS

| | | | |
|---|---|---|---|
| 3,626,286 | 12/1971 | Rauchwerger | 324/61 R |
| 3,771,548 | 11/1973 | Rauchwerger | 137/392 |
| 4,288,742 | 9/1981 | Walsh | 324/61 R |
| 4,459,474 | 7/1984 | Walton | 235/380 |
| 4,471,345 | 9/1984 | Barrett, Jr. | 340/572 |
| 4,693,419 | 9/1987 | Weintraub et al. | 239/63 |
| 4,801,865 | 1/1989 | Miller et al. | 324/65 R |
| 5,136,262 | 8/1992 | Spencer | 331/135 |
| 5,148,125 | 9/1992 | Woodhead et al. | 331/135 |
| 5,148,126 | 9/1992 | Spencer | 331/135 |
| 5,235,319 | 8/1993 | Hill et al. | 340/573 |
| 5,260,666 | 11/1993 | Dishman et al. | 324/664 |
| 5,418,466 | 5/1995 | Watson et al. | 324/668 |
| 5,424,649 | 6/1995 | Gluck et al. | 324/667 |
| 5,445,178 | 8/1995 | Feuer | 137/1 |
| 5,479,104 | 12/1995 | Cambell | 324/690 |
| 5,488,311 | 1/1996 | Kamioka et al. | 324/674 |
| 5,559,520 | 9/1996 | Barzegar et al. | 342/357 |
| 5,631,418 | 5/1997 | Stuns et al. | 73/29.01 |
| 5,859,536 | 1/1999 | Stockton | 324/664 |

FOREIGN PATENT DOCUMENTS

| | | | |
|---|---|---|---|
| 0 716 808 A2 | 6/1996 | European Pat. Off. | A01N 37/10 |

*Primary Examiner*—Diep N. Do
*Attorney, Agent, or Firm*—Sheridan Ross P.C.

[57] ABSTRACT

A device for sensing changes in the permittivity of a sample of a monitored medium is disclosed. The monitored medium is exposed to an environment having one or more elements. The device includes an LC oscillator circuit and an output circuit coupled thereto. The LC circuit contains an inductance element and a capacitance element and has a resonance frequency which is dependent upon the permittivity of the sample. The capacitance element includes first and second conductive elements surrounded by an insulating dielectric material so that the first and second conductive elements are prevented from being exposed to one or more elements of the environment of the sample. The output circuit is adapted to output a signal representative of the permittivity of the sample. A method of determining changes in the permittivity of a sample of a medium is also disclosed. The method includes the steps of: (1) disposing a permittivity sensor having an LC oscillator circuit into the medium, the LC oscillator circuit having a resonance frequency dependent upon the permittivity of the sample, wherein the capacitance element includes first and second conductive elements surrounded by an insulating dielectric material, the insulating dielectric material being surrounded by the sample; and, (2) outputting a signal representative of the permittivity of the sample.

42 Claims, 7 Drawing Sheets

SENSOR FOR SENSING CHANGES IN THE PERMITTIVITY OF A MEDIUM IN WHICH IT IS DISPOSED

FIELD OF THE INVENTION

The present invention is directed to sensing devices, and more particularly, to devices which sense permittivity changes of a monitored medium.

BACKGROUND OF THE INVENTION

It has been recognized that the permittivity of certain (generally homogeneous) media varies with changes in the homogeneity of the media. Generally, an increase (or decrease) in the content of a sample of first material relative to a sample of a second material; wherein the permittivity of the first material is sufficiently different compared to the permittivity of the second material, will generally cause a change (either an increase or a decrease) in the permittivity of the homogeneous (or near homogeneous) media formed by both samples uniformly mixed.

In the case of water and soil, a variety of devices have been developed to sense the moisture content of soil. These devices can be used, for example, to control irrigation or drainage systems. In such devices, a sample of soil having a predetermined volume is monitored and its moisture content is sensed. The moisture content of the soil surrounding the sample is assumed to be representative of the moisture content of the soil sample itself. It is important, therefore, that the information provided by the devices is based solely on the moisture content of the soil rather than variations in some other parameters which are specific to the soil sample but not to the surrounding soil.

Conventional sensors have typically included a pair of parallel plates which surround a soil sample. The combination of the parallel plates and soil sample form a variable capacitor that is coupled to an electronic circuit. By being positioned between the parallel plates, the soil operates as the capacitor's dielectric. Since variations in the soil's moisture content causes variations in its permittivity, the value of the capacitor changes with variations in the soil's moisture content.

In order to take advantage of this known phenomenon, some conventional soil moisture sensors have incorporated the aforementioned variable capacitors into either resistor-capacitor ("RC") or inductor-capacitor ("LC") oscillator circuits. As is well known, the oscillation frequencies of RC and LC circuits vary with the capacitance value of the capacitor if all other parameters are held constant. Hence, some have thought that they can accurately determine the moisture content of a soil sample by detecting the oscillation frequencies of an RC or LC circuit where the capacitor of the circuit incorporates a pair of parallel plates which sandwich the soil sample therebetween. Prior RC and LC circuits, however, have not been able to consistently measure the oscillation frequency attributable to the moisture content of the medium being monitored for several reasons.

For example, in the case of RC circuits, variations in the oscillation frequency of RC circuits are not only attributable to the permittivity of the sample but are also attributable to the sample's conductivity. The sample's conductivity can be drastically affected by the soil's salinity, which can vary greatly over relatively small distances. Furthermore, the amount of the soil's conductive components in a sample, which can also vary greatly over relatively small distances due to its generally non-homogeneous nature, can also affect its conductivity.

Because of these non-uniformities, it is nearly impossible to factor out the effects of the soil's conductivity from the effects of the soil's permittivity. Accordingly, RC circuits are not particularly well-suited for measuring the moisture content of soil.

Due to the problems associated with RC oscillator circuits, there has been a recent trend to replace them with LC oscillator circuits, whose resonance frequency is relatively independent of the conductivity of its dielectric, when sensing the moisture content of soil. U.S. Pat. No. 5,445,178 to Feuer, for example, discloses a moisture sensor which employs an LC oscillator circuit. The sensor includes a pair of elongated sensor elements which have a rectangular cross-section, are spaced apart by a gap and are coupled to an electronic module. A pair of braces are used to maintain a uniform gap width along the length of the sensor elements. The sensor elements, which function as capacitor plates, are installed in soil by pushing or burying them so that the soil is between and around the sensor elements. The soil, therefore, functions as the dielectric of the capacitor.

As is well-known, U.S. Pat. No. 5,445,178 discloses that the LC oscillator defines a resonance frequency $f_o$ dependent upon the value L of the inductor and the value C of the capacitor based generally on the equation:

$$f_o = \frac{1}{2\pi\sqrt{LC}}$$

By choosing an appropriate inductance value, one can set the frequency range of an LC oscillator. In the preferred embodiments of U.S. Pat. No. 5,445,178, the inductance value was chosen so that the LC oscillator circuit operates in the frequency range of approximately 10 kHz to 10 MHZ. Oscillators which operate in that frequency range, however, suffer from problems, in that, the resonance frequency of the LC circuit is not properly indicative of the moisture content of the soil sample.

Specifically, it has been found that, at low frequencies, capacitors comprised of dielectrics having characteristics similar to soil are subjected to the Maxwell-Wagner effect (also known as interfacial polarization), whereby charges having a polarity opposite to the polarity of the capacitor's plates "line-up" along the plates. In an LC oscillator circuit, the polarity of the capacitor's plates varies with its oscillation frequency. At low oscillation frequencies, the above-described charges can respond quickly enough to "line-up" along the plates. Consequently, as will be understood by those skilled in the art, the resulting frequency of the system is such that the calculated permittivity of the dielectric appears different from its actual permittivity.

It has been found that at frequencies higher than 27 MHZ, the charges cannot follow the polarization changes in the capacitor's plates. Therefore, capacitors operating at such frequencies are not subjected to the Maxwell-Wagner effect. Because the preferred embodiment of the device disclosed in U.S. Pat. No. 5,445,178 operates at frequencies substantially less than 27 MHZ, it is believed that the device suffers from the Maxwell-Wagner effect and is incapable of delivering accurate results consistently.

The device disclosed in U.S. Pat. No. 5,445,178 also suffers from a number of other deficiencies. First, because the sensor elements are metallic and exposed (i.e., it has no insulating dielectric sheath), the device is temperature dependent. Second, both the sensor elements and the spacers must be specially machined and, therefore, are relatively costly. Third, because the spacers must properly fit the sensor elements, both the sensor elements and the spacers must be manufactured according to relatively tight tolerances. Fourth, the sensor elements, because they are made of metal, are susceptible to corrosion and decomposition when placed in acidic mediums. Fifth, because of the surface area spanned by the plates and their lack of flexibility, the device is relatively difficult to place in the medium. Finally, the combination of the mechanical and electrical components described in U.S. Pat. No. 5,445,178 yields a device which is relatively complex and expensive.

Another patent which discloses an LC oscillator is U.S. Pat. No. 5,418,466 to Watson et al. U.S. Patent No. 5,418,466 is directed to a moisture and salinity sensor. The device includes a support frame for accommodating an array of sensors located within an access tube which has been inserted into a prepared hole in the soil. The sensors include a capacitive element in the form of upper and lower conductive rings which are disposed in spaced relationship to each other to maintain a constant air gap. The LC oscillator circuit changes its resonance frequency in response to moisture changes in the soil under the capacitive element's "sphere of influence."

Although the device of U.S. Pat. No. 5,418,466 is designed to operate at frequencies above 27 MHZ, like the device disclosed in U.S. Pat. No. 5,445,178, the device of U.S. Pat. No. 5,418,466 suffers from a number of deficiencies. First, the sensor elements, access tube, support and conductive rings must be specially machined. Second, because all of the aforementioned elements must fit together, they must be made under relatively tight tolerances. Third, devices of this kind seem to suffer from mechanical stress and shock during installation. The resulting device, including its mechanical and electrical components, therefore, is relatively complex and expensive.

Accordingly, there is a need for a permittivity sensor which overcomes many, if not all, of the aforementioned deficiencies of the prior systems.

It would be advantageous to provide a permittivity sensor which includes one or more of the following advantages: (1) relatively inexpensive and not complex; (2) not subject to relatively tight tolerances; (3) capable of being manufactured using "off-the-shelf" products; (4) not temperature dependent; (5) resistant to acidic mediums; (6) tolerant to mechanical shock; and, (7) easy to place in a monitored medium.

SUMMARY OF THE INVENTION

In accordance with the present invention, one embodiment of the permittivity sensor includes an LC oscillator circuit and an output circuit coupled thereto. The LC circuit contains an inductance element and a capacitance element and has a resonance frequency which is dependent upon the permittivity of a sample of a monitored medium. The monitored medium is located in an environment having one or more elements (e.g., temperature variations, moisture variations and the like). The capacitance element includes first and second conductive elements surrounded and separated by an insulating dielectric material so that the first and second conductive elements are prevented from being exposed to one or more elements of the environment of the sample. The output circuit is adapted to output a signal representative of the permittivity of the sample.

A method of determining changes in the permittivity of a sample of a medium is also disclosed. The method includes the steps of: (1) disposing a permittivity sensor having an LC oscillator circuit into the medium, the LC oscillator circuit having a resonance frequency dependent upon the permittivity of the sample, wherein the capacitance element includes first and second conductive elements surrounded by an insulating dielectric material, the insulating dielectric material being surrounded by the sample; and, (2) outputting a signal representative of the permittivity of the sample.

Other features and advantages of the invention will be apparent from the following specification taken in conjunction with the following drawings.

DETAILED DESCRIPTION OF THE PREFERRED EMBODIMENT

Figure 1:
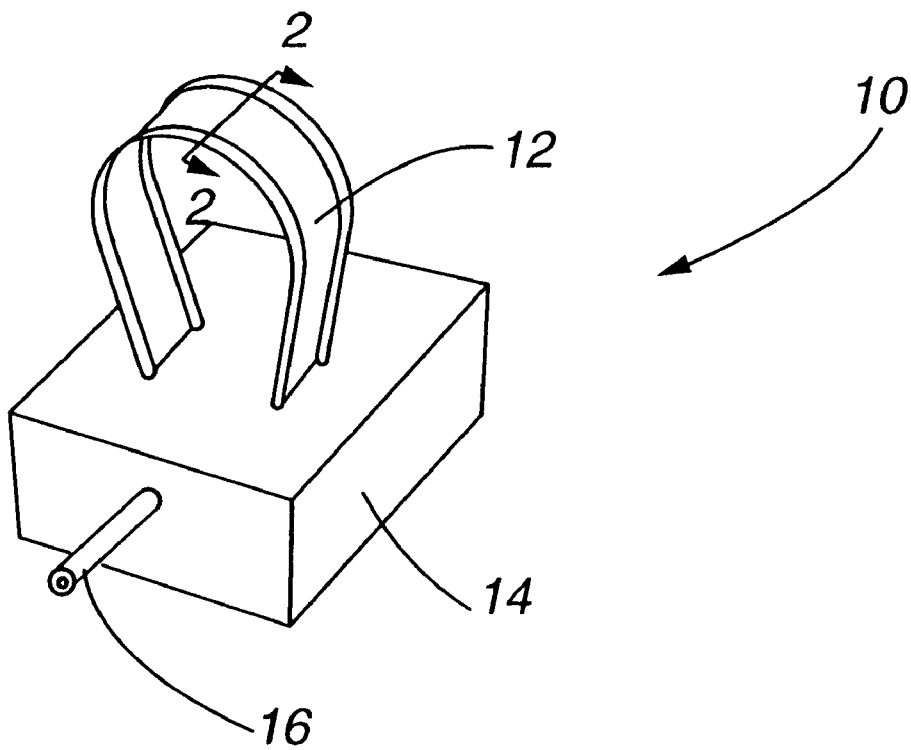
FIG. 1 is a diagrammatic representation of a perspective view of the permittivity sensor of the present invention.

A permittivity sensor, generally designated 10, is illustrated in FIG. 1. The permittivity sensor 10 includes a sensor element 12, an electronic module 14 and a transmission line 16. As depicted in the figure, both the sensor element 12 and the transmission line 16 are coupled to the electronic module 14.

In operation, the sensor element 12 is disposed within a medium to be monitored and operates as a capacitor. A portion (or sample) of the medium to be monitored acts as the capacitor's dielectric. The sensor element 12 cooperates with the electronic module 14 to determine changes in the permittivity of the sample of monitored material. This information is then communicated to the transmission line 16. In some applications of the invention, it is assumed that the permittivity of the monitored material immediately surrounding the sample is nearly the same as the permittivity of the sample.

The sensor element 12 is preferably made of what is conventionally referred to as twin-lead cable or antenna wire. In the preferred embodiment, the characteristic impedance of the sensor element 12 is 300 ohms. Accordingly, some refer to the twin-lead cable of the preferred embodiment as 300 ohm antenna wire.

It should be noted, however, that the characteristic impedance of the sensor element 12 is not to be limited to 300 ohms in other embodiments. For instance, the characteristic impedance of the twin-lead cable could be 75 ohms or some other value. Preferably, the twin-lead cable which comprises the sensor element 12 should be one that is commercially available and relatively inexpensive.

Figure 2:
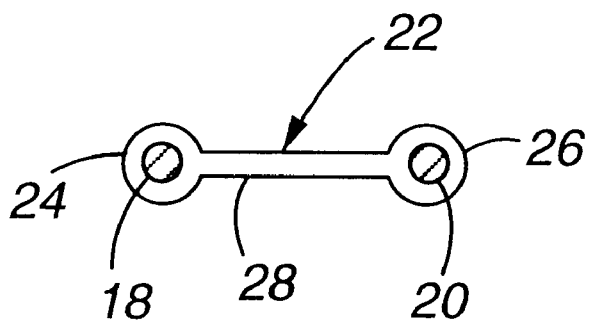
FIG. 2 is a diagrammatic representation of a cross-sectional view of the sensor element 12 of FIG. 1 taken along line 2—2.

With reference to FIGS. 1 and 2, the sensor element 12 includes first and second conductive elements 18,20 having an insulating dielectric material 22 molded therearound. As shown in FIG. 2 (which is a cross-sectional view of FIG. 1 taken along line 2—2), the first and second conductive elements 18,20 are comprised of flexible cylindrical wires which respectively run along first and second edges 24,26 of the insulating dielectric material 22.

The insulating dielectric material 22 has a central section 28 which serves to maintain the first and second conductive elements 18,20 in a generally equidistant relationship with respect to one another. The geometry between the first and second conductive elements 18,20 is important with respect to the operation of the conductive elements 18,20 as capacitor "plates."

In the preferred embodiment, the insulating dielectric material 22 is made of polyethylene. However, the insulating dielectric material 22 may be made up of a variety of substances including, for example, polystyrene, Teflon, polyester, plastic resins, Mylar or any other insulating material with similar dielectric properties. The insulating dielectric material 22 serves to protect the first and second conductive elements 18,20 from temperature variations, exposure to acidic materials and mechanical shock. In addition, its flexibility assists in its installation and in the manufacturing of the whole system.

Figure 3:
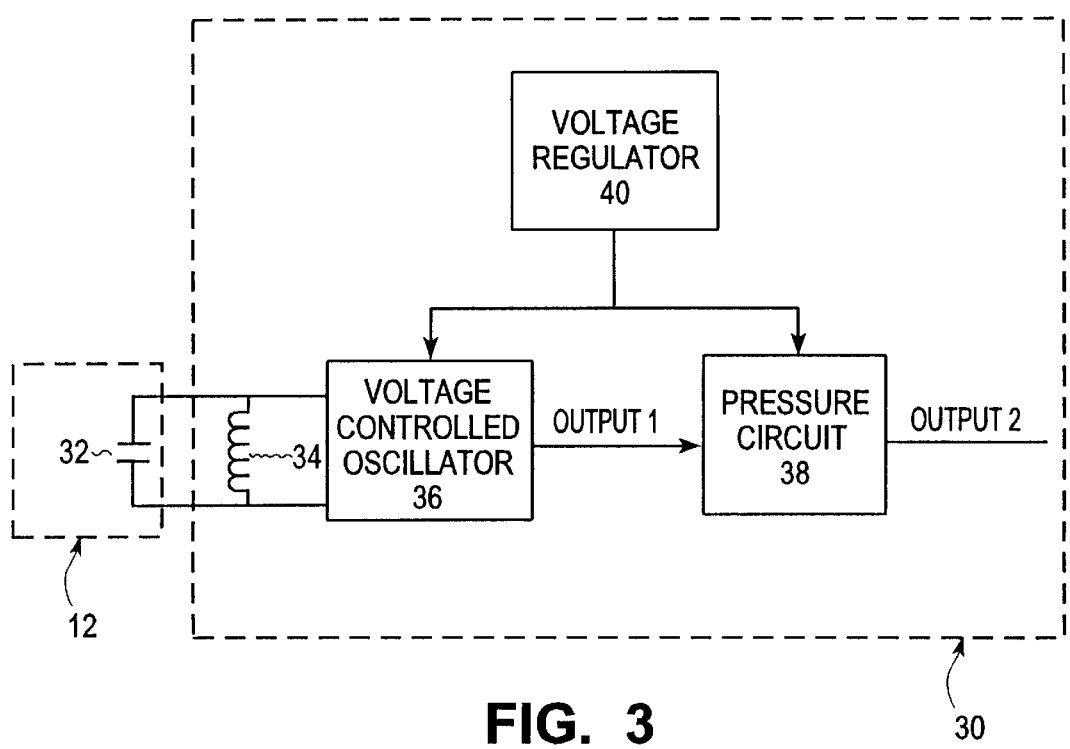
FIG. 3 is a block diagram of the electronic circuitry of the present invention.
Figure 4:
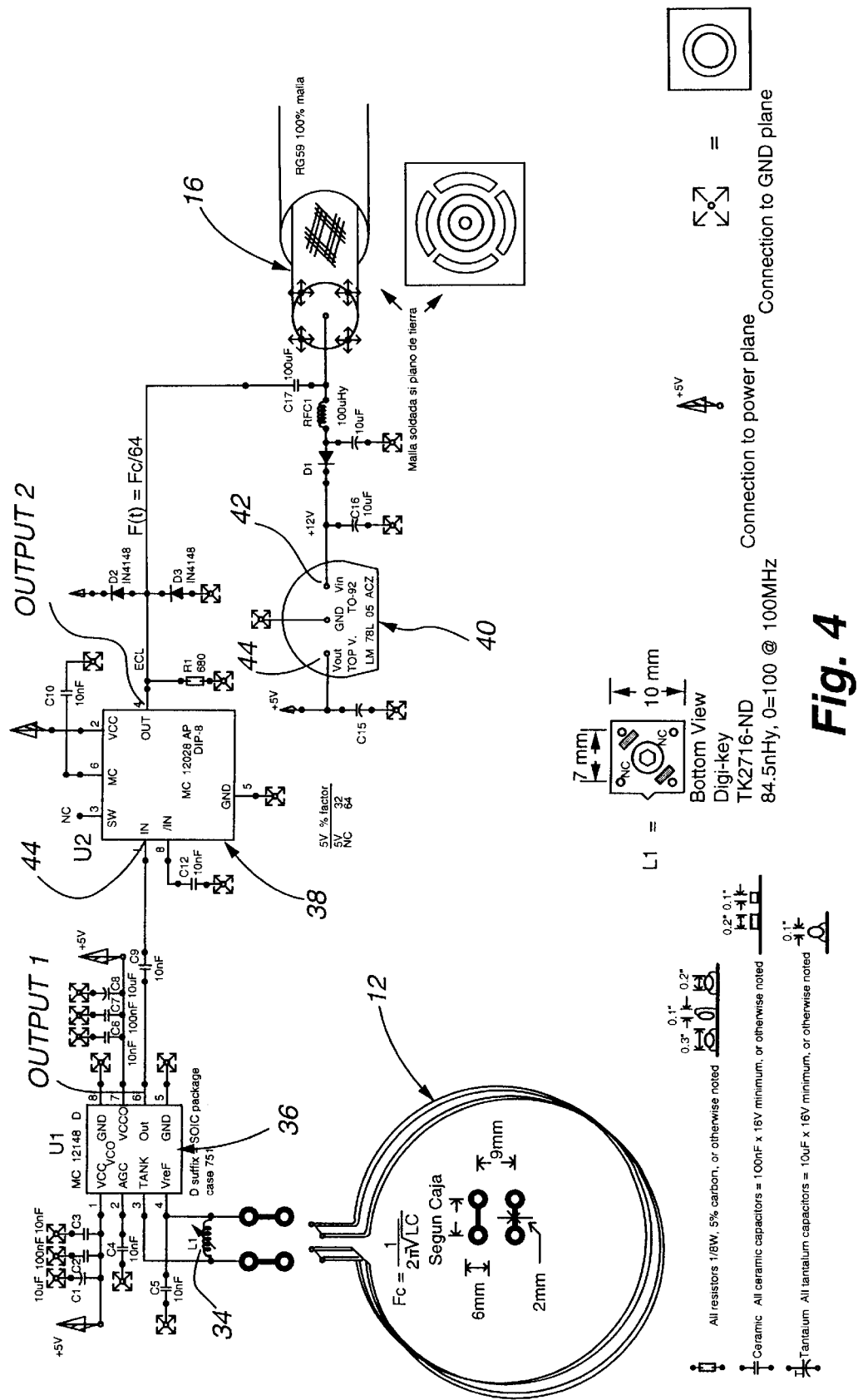
FIG. 4 is an electrical schematic diagram of the electronic circuitry of the present invention.

The electronic module 14 includes electronic circuitry 30 (shown in dashed lines in FIG. 3) which, in combination with the sensor element 12, serves to determine changes in the permittivity of the sample of material surrounding the sensor element 12. FIG. 3 is a block diagram of the electronics of the permittivity sensor 10 in which the sensor element 12 (depicted as a capacitor 32) is surrounded by a first set of dashed lines having the reference numeral 12 associated therewith and the electronic circuitry 30 of the electronic module 14 is surrounded by a second set of dashed lines having the reference numeral 30 associated therewith. FIG. 4 is an electrical schematic of the electronics of the permittivity sensor 10.

As depicted in the block diagram, the electronic circuitry 30 includes an inductor 34, a voltage controlled oscillator 36, a prescaler circuit 38 and a voltage regulator 40. The capacitor 32 (formed by a combination of the sensor element 12 and a sample of the medium being monitored) and the inductor 34 combine to form an LC oscillator having a resonance frequency $f_o$ where:

$$f_o = \frac{1}{2\pi\sqrt{LC}}$$

Because the value of the inductor 34 is substantially constant, the magnitude of the resonance frequency will be inversely proportional to the capacitance value of the capacitor 32. Furthermore, because all of the variables used to obtain the capacitance value, except the value pertaining to the sample's permittivity, are held constant, the magnitude of the resonance frequency $f_o$ will be inversely proportional to the permittivity of the monitored medium, as will be explained in further detail below.

The capacitance formula, which is based upon a capacitor having parallel plates of an infinite size, is equal to kA/d where k is the value of the dielectric constant, A is the area of the overlay of the plates and d is the distance between the plates. As will be understood by those skilled in the art, if both A and d are held constant, the capacitance value will be directly proportional to the value of dielectric constant k. The permittivity of the dielectric is equal to the dielectric constant k multiplied by the permittivity of free space $e_o$ ($e_o$=8.85×10$^{-12}$ F/m). Hence, the capacitance value will be directly proportional to the permittivity of the sample.

We can use the capacitance formula, discussed above, as a model for the capacitor 34 defined by the sensor element 12 and a sample of the monitored medium. Because both the area of overlay (A) and the spacing (d) between the first and second conductive elements 18,20 are held constant for a given sensor, the capacitance value will be directly proportional to the value of the permittivity of the sample of the monitored medium. Accordingly, the resonance frequency $f_o$ of the LC oscillator circuit will be inversely proportional to the permittivity of the sample of the monitored medium.

The first and second conductive elements 18,20 form a capacitor having a dielectric comprised of (1) the medium surrounding the sensor element 12; and, (2) the insulating dielectric 22 (see FIGS. 1 and 2). Because the permittivity of the insulating dielectric 22 is relatively consistent over variations in the permittivity of most mediums, its contribution to the permittivity measurement is simply factored out.

As shown in FIG. 3, the voltage regulator 40 is coupled to voltage controlled oscillator 36 and prescaler circuit 38 so that it can provide power to each. More specifically, with reference to FIG. 4, the voltage regulator 40 is coupled to transmission line 16 which delivers a power signal in the form of a 12 V supply to the voltage regulator's input 42. As is conventionally known, the voltage regulator 40, through its internal functions, makes a 5 V biasing voltage available at its output 44. The voltage regulator's output 44 is coupled to voltage controlled oscillator 36 and prescaler 38 to provide them with their required biasing voltages.

Referring again to FIG. 3, the LC oscillator circuit formed by capacitor 32 and inductor 34 has a resonance frequency $f_o$ where:

$$f_o = \frac{1}{2\pi\sqrt{LC}}$$

Consequently, a signal having a frequency equal to $f_o$ is delivered at the output (output 1 in FIG. 3) of the voltage controlled oscillator 36.

In the preferred embodiment, $f_o$ is chosen to be around 200 MHZ so that the circuit does not suffer from the Maxwell-Wagner effect. As one skilled in the art will appreciate, the range of the resonance frequency $f_o$ can be set by choosing an appropriate value of the inductor 34. That is, by knowing the permittivity ranges of the monitored medium, the range of the resonance frequency can be set by the inductor 34 through use of the resonance frequency formula for LC oscillator circuits.

Returning again to FIG. 3, the output (output 1) of the voltage controlled oscillator 36 is coupled to the input 44 of the prescaler circuit 38. The internal operations of the prescaler circuit 38 yield an output signal (output 2) having a frequency which is a fraction of the resonance frequency $f_o$. In the preferred embodiment, the prescaler circuit 38 produces an output signal having a frequency which is 1/64th of the frequency of its input signal. Accordingly, the frequency of the output signal (output 2) of the prescaler circuit 38 is approximately 3 MHZ.

The purpose of the prescaler circuit 38 is to deliver a signal to the transmission line 16 at a relatively low frequency so that the transmission line 16 can be made of a relatively standard cable. In the preferred embodiment, the transmission line is a coaxial shielded cable having an impedance of 75 ohms. Of course, the invention is not limited to a transmission line having an impedance of 75 ohms; rather, the transmission line may have an impedance of 50 ohms or some other value.

The other components which make up the electronic circuitry of the preferred embodiment of the present invention are shown in FIG. 4, the values of which will be appreciated by those skilled in the art. Of special note are capacitor $C_{17}$ and inductor RFC1, which allow the center conductor of the coaxial cable, which preferably forms the transmission line 16, to (1) deliver 12 V DC to the voltage regulator; and, (2) receive the AC output of the prescaler.

Specifically, capacitor $C_{17}$ operates as a dc blocker by preventing the current corresponding with the 12 V DC power source from being inappropriately delivered to the prescaler circuit 38 and ensures that it is delivered to the voltage regulator 40. Similarly, the inductor RFC1 operates as an RF choke by preventing the output of the prescaler circuit 38 (which, in the preferred embodiment, has a frequency of about 3 MHZ) from being delivered to the voltage regulator and ensures that it is delivered to the center conductor of the transmission line 16.

It should be noted that, in one embodiment, the voltage controlled oscillator 36 is an integrated circuit manufactured by Motorola having part no. MC 12148 D; the prescaler 38 is an integrated circuit manufactured by Motorola under part no. MC 12028 AP; and, the voltage regulator 40 is an integrated circuit manufactured by National Semiconductor having part no. LM 78L 05 ACZ. All of these integrated circuits are commercially available, such as from Newark Electronics of Chicago, Ill.

It should be noted that Motorola manufactures a family of voltage controlled oscillator integrated circuits which have part numbers which begin with MC 121xx. Similarly, Motorola also manufactures a family of prescaler integrated circuits which have part numbers which begin with MC 120xx. Accordingly, the present invention is not intended to be limited to the integrated circuits used in the above-mentioned embodiment, nor is it intended to be limited solely to integrated circuits manufactured by Motorola (or National Semiconductor in the case of the voltage regulator 40).

Figure 5:
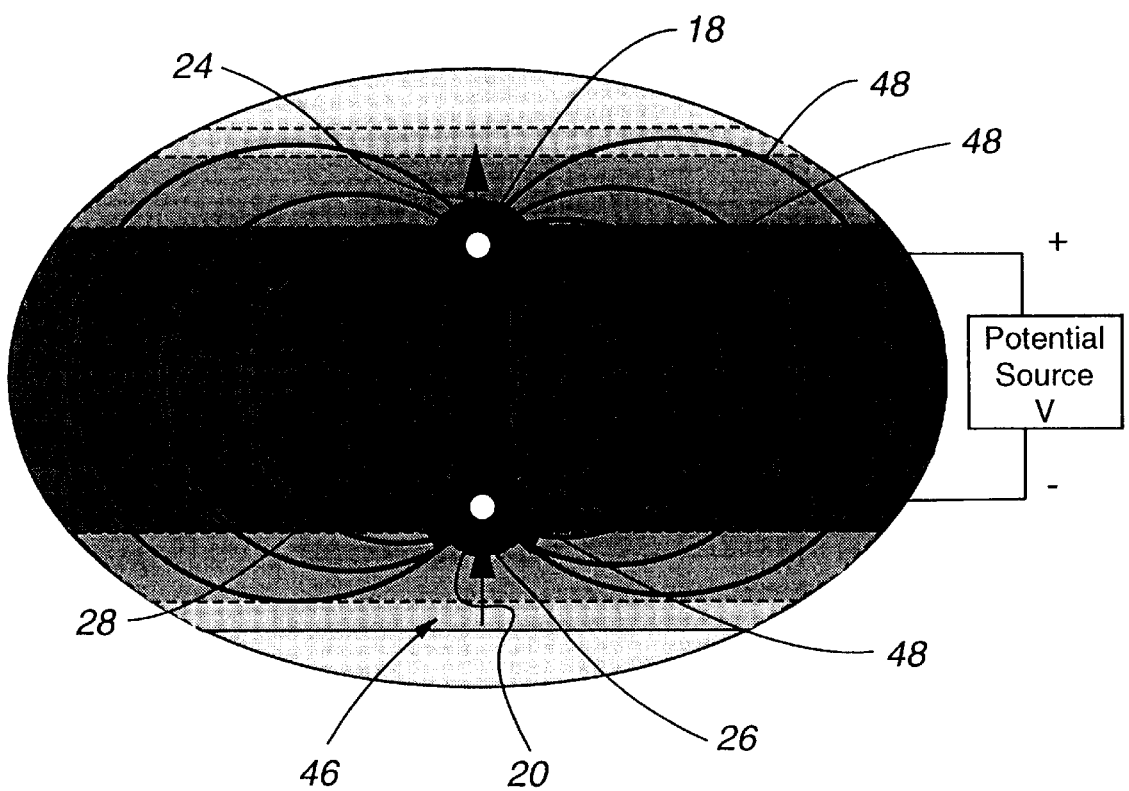
FIG. 5 is a diagrammatic representation of the electric field lines set up around the sensor element 12 of the present invention.

FIG. 5 shows the cross-section of the sensor element 12 of FIG. 2 rotated clockwise 90 degrees and disposed within a medium to be monitored 46. Electric flux lines 48, in the form of arc-shaped segments, are generated between the first and second conductors 18,20. As will be understood by those skilled in the art, the sample size of the monitored medium 46 is dependent upon the outer boundary of the electric flux lines 48.

As can be gleaned from the above description, the permittivity sensor 10 can monitor the permittivity of a wide variety of first and second materials. Particular examples of first and second materials are those of water and soil, lixiviant (e.g., sulfuric acid and cyanide) and mineral ore, gasoline and soil, etc. A first material for which the permittivity sensor 10 has found particular applicability is soil.

The combination of soil and water has a permittivity which varies between approximately $5e_o$ and $80e_o$. An increase in the moisture content of soil will generally cause an increase in its permittivity. Accordingly, by measuring the permittivity of soil using the device 10, one can determine its moisture content.

Figure 6:
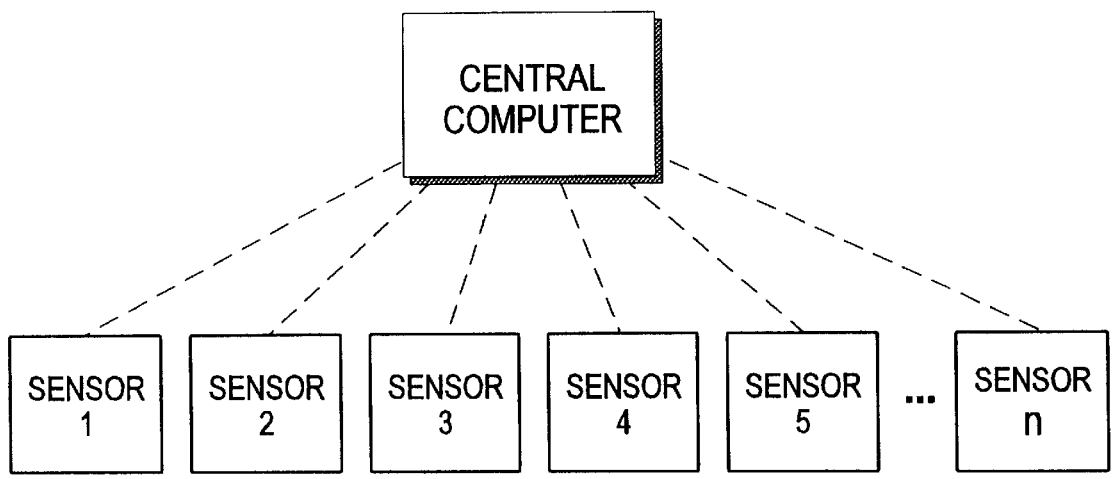
FIG. 6 is a block diagram of a system which obtains permittivity data from a plurality of permittivity sensors.

In certain instances, it may be necessary to obtain many samples of the medium both at varying distances beneath the soil's surface as well as at varying locations near the soil's surface. For example, the moisture content of portions of farmland may vary due to elevational differences and slope differences in the land, for instance. In such case, a plurality of permittivity sensors 10 might be placed at different depths and locations around the farmland. The permittivity information would then be transmitted to a central computer station (shown in FIG. 6) which would analyze the information and could provide a recommended course of action or could automatically divert water towards or away from a particular piece of land.

The permittivity information could be transmitted in a variety of manners including coaxial cable, radio-wave communication, fiber optics cable and the like. In the preferred embodiment, coaxial cable is the transmission medium of choice.

It should be understood that the present invention is not limited to sensing the moisture content of or moisture changes in soil. Rather, the present invention has a wide variety of other applications.

For example, the present invention can be used in heap leaching procedures. As is well-known, heap leaching involves the extraction of minerals from a mound of ore using certain liquids (e.g., sulfuric acid or cyanide) that are percolated through the mound. In such case, permittivity sensors 10 could be placed in varying vertical and horizontal locations throughout the mound to determine, for example, (1) whether the liquid has missed a certain area(s) of the mound, and/or (2) the speed at which the liquid is passing through the mound. Furthermore, since the mounds of ore are usually placed over an impermeable layer, permittivity sensors 10 could also be placed in a medium underneath the impermeable layer to detect leaks in the impermeable layer. For example, if the permittivity of the medium underneath the impermeable layer changed by an amount greater than a predetermined amount, the sensor would alert of a leak.

In another application, the present invention can be used to detect gasoline leaks. For example, most gas stations have gasoline tanks which are used to store large volumes of gasoline to be dispensed to customers. Such tanks are generally placed in beds of impermeable clay to avoid seepage if the tank ruptures. By placing the permittivity sensors 10 of the present invention in and around the beds surrounding the tanks, leaks in the gas tanks can be detected.

In a similar way, the present invention can be used to detect leaks in liners used for impoundment ponds. In some instances, the materials leaking through impoundment pond liners are highly corrosive. Fortunately, another advantage of the permittivity sensors 10 of the present invention is that they can sustain exposure to highly corrosive materials for periods of time generally long enough to indicate significant permittivity changes. This is due, in part, to the protective dielectric material 22 which surrounds the first and second conductive elements 18,20.

Another one of the significant advantages of the permittivity sensors 10 of the present invention is that, because they are so inexpensive to manufacture, they do not need to be dug-out after their use. Furthermore, if one wanted to dig to the locations where the permittivity sensors were placed, care would not need to be exercised in preserving the sensors in that the sensors could be inexpensively replaced.

Figure 7:
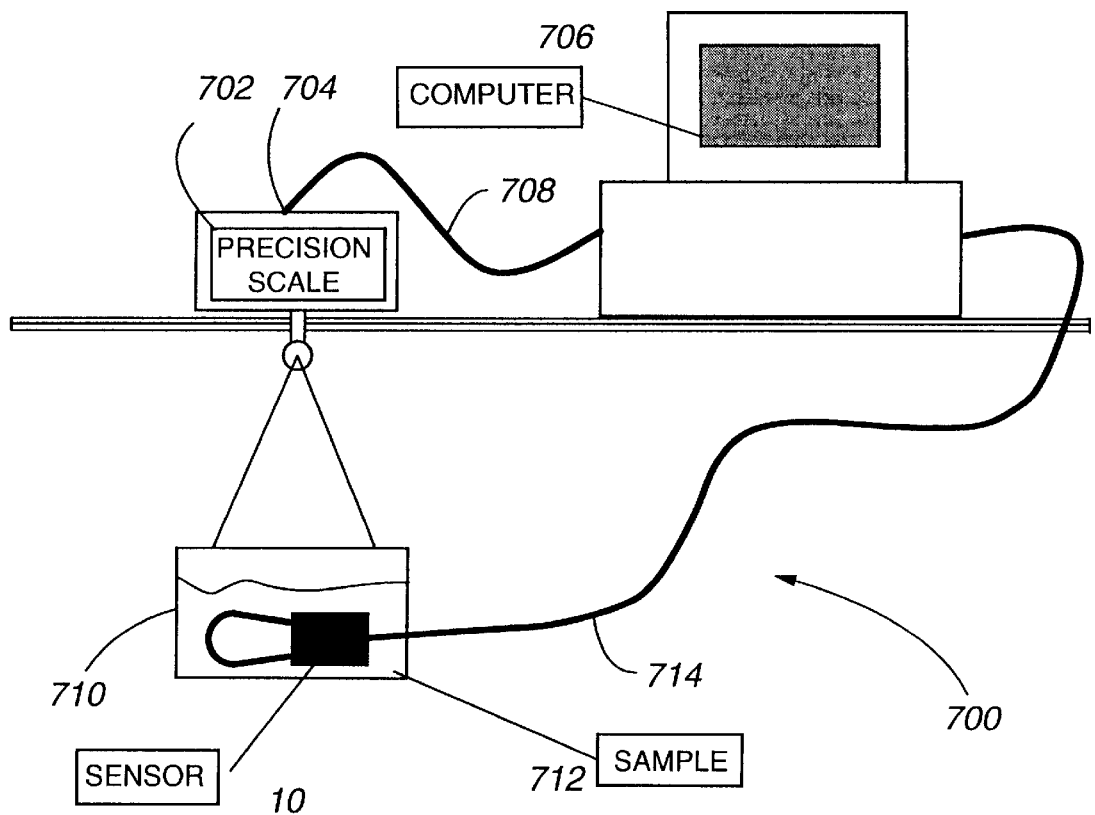
FIG. 7 is a diagrammatic representation of a set-up used to calibrate a permittivity sensor; and, FIG. 8 is a perspective view of another embodiment of the sensor element of the present invention.

FIG. 7 shows a set-up 700 for calibrating the permittivity sensor 10. Specifically, the set-up 700 is used to correlate the resonance frequency $f_o$ of the sensor 10 to the moisture content of a mixture, as will be discussed in more detail below.

The set-up 700 includes a precision scale 702 having an output 704 which is coupled to a computer 706 via a first conductor 708. A container 710 is suspended from the precision scale 702. Accordingly, the output 704 of the precision scale 702 (which is delivered to the computer 706) reflects the weight of the container 710 plus any materials contained therein. The container 710 is used to hold a predetermined portion 712 of the medium to be monitored. A permittivity sensor 10 is placed within the predetermined portion 712 and is coupled to the computer 706 via a second conductor 714 which receives an output signal representative of the resonance frequency $f_o$ of the permittivity sensor 10.

To correlate the resonance frequency $f_o$ of the sensor 10 to the moisture content of the mixture, first, a first material (e.g., soil) is placed within the container 710 and both the weight of the first material and the resonance frequency $f_o$ of the sensor 10 are measured. Next, a second material, usually in the form of a fluid (e.g., water), is added to the first material. The weight percent of the second material relative to the combination of the first and second materials is then determined. In addition, the resonance frequency $f_o$ of the sensor is also determined. These steps are repeated until a correlation between the frequency of the LC oscillator circuit to the weight percent of the second material relative to the first material (i.e., in this case the moisture content of soil) can be developed. The slope of the curve will be equal to a correlation factor between the resonance frequency $f_o$ and the moisture content of the medium. Tests have shown a consistent polynomial relationship between the resonance frequency $f_o$ and the moisture content of the medium.

Figure 8:
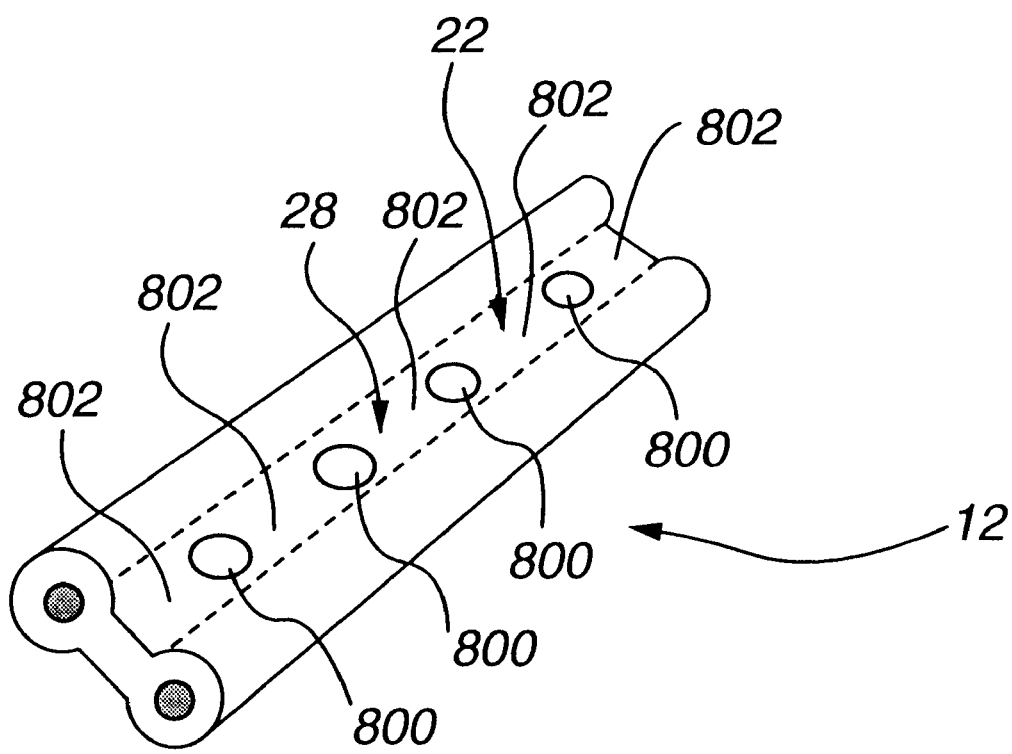

FIG. 8 depicts another embodiment of the sensor element 12 originally shown FIGS. 1 and 2. More specifically, the embodiment of the sensor element 12 shown in FIG. 8 differs from the embodiment shown in FIGS. 1 and 2 in that the central section 28 of the insulating dielectric material 22 of FIG. 8 has a plurality of apertures 800 therein. The plurality of apertures 800 decrease the rigidity of the dielectric material 22 so that the sensor element 12 may be bent more easily. Additionally, the plurality of apertures 800 may slightly enhance the performance of the permittivity sensor 10. Those portions 802 of the central section 28 where the plurality of apertures 800 are not present prevent a volume of the medium from being disposed between the first and second conductive elements 18,20.

Finally, it should be noted that the present invention is not limited to a sensor having a sensor element 12 which is flexed in an arch shape as shown in FIG. 1. Instead, the sensor element 12 could be comprised of, for example, long strips of antenna wire. In such case, the present invention could be used as a level meter as will be understood by those skilled in the art.

It will be understood that the invention may be embodied in other specific forms without departing from the spirit or central characteristics thereof. The present examples and embodiments, therefore, are to be considered in all respects as illustrative and not restrictive, and the invention is not intended to be limited to the details given herein.

What is claimed is:

1. A device for sensing changes in the permittivity of a sample of a medium exposed to an environment having one or more elements, the device comprising:

an LC oscillator circuit having an inductance element and a capacitance element, the inductance element having a relatively constant value, L, and the capacitance element having a variable value, C, wherein the value of the capacitance element is dependent upon the permittivity of the sample in which the capacitance element is disposed, the LC oscillator circuit having a resonance frequency dependent upon the value of the inductance element and the value of the capacitance element given by the relationship $1/(2\pi(LC)^{1/2})$, wherein the capacitance element includes first and second conductive elements substantially surrounded by an insulating dielectric material so that the first and second conductive elements are substantially prevented from being exposed to one or more elements of the environment of the sample and so that the first and second conductive elements are prevented from contacting one another, the inductance element having a first lead and a second lead, the first conductive element being electrically coupled to the first lead of the inductance element and the second conductive element being electrically coupled to the second lead of the inductance element; and, an output circuit coupled to the LC oscillator circuit adapted to output a signal representative of the permittivity of the sample based upon the resonance frequency of the LC oscillator circuit, wherein changes in the output signal are indicative of changes in the permittivity of the sample.

2. The device of claim 1 wherein the insulating dielectric material spans between the first and second conductive elements and prevents a volume of the medium from being disposed therebetween.

3. The device of claim 1 wherein the first and second conductive elements along with the insulating dielectric are flexed so that they are shaped like an arch.

4. The device of claim 1 wherein the insulating dielectric is selected from the group consisting of polyethylene, polystyrene, Teflon, polyester, plastic resins and Mylar.

5. The device of claim 1 wherein the value of the inductor element is selected so that the resonance frequency of the LC oscillator is greater than 27 MHZ.

6. The device of claim 5 wherein the value of the inductor element is selected so that the resonance frequency is around 200 MHZ.

7. The device of claim 5 wherein the output circuit includes a frequency divider.

8. The device of claim 7 wherein the output signal has a frequency of about 3 MHZ.

9. The device of claim 1 wherein the output circuit is coupled to an output transmission line.

10. The device of claim 9 wherein the transmission line is coupled to a computer, the transmission line delivering the output signal to the computer.

11. The device of claim 1 wherein the insulating dielectric material maintains the first and second conductors in an equidistant relationship relative to one another.

12. The device of claim 11 wherein the insulating dielectric material maintains the first and second conductors in a generally parallel relationship to one another.

13. The device of claim 1 wherein the output circuit includes a voltage controlled oscillator which generates a first output signal having a frequency equal to the resonance frequency.

14. A device for sensing changes in the permittivity of a sample of a medium exposed to an environment having one or more elements, the device comprising:

an LC oscillator circuit having an inductance element and a capacitance element, the inductance element having a relatively constant value, L, and the capacitance element having a variable value, C, wherein the value of the capacitance element is dependent upon the permittivity of the sample in which the capacitance element is disposed, the LC oscillator circuit having a resonance frequency dependent upon the value of the inductance element and the value of the capacitance element given by $1/(2\pi(LC)^{1/2})$, wherein the capacitance element includes a twin-lead cable having first and second conductive elements, wherein twin lead cable includes a dielectric material which substantially surrounds each of its leads, the inductance element having a first lead and a second lead, the first conductive element being electrically coupled to the first lead of the inductance element and the second conductive element being electrically coupled to the second lead of the inductance element; and, an output circuit coupled to the LC oscillator circuit adapted to output a signal representative of the permittivity of the sample based upon the resonance frequency of the LC oscillator circuit, wherein changes in the output signal are indicative of changes in the permittivity of the sample.

15. The device of claim 14 wherein the twin-lead cable has a characteristic impedance of 300 ohms.

16. The device of claim 14 wherein the twin-lead cable has a characteristic impedance of 75 ohms.

17. The device of claim 14 wherein the insulating dielectric material spans between the first and second conductive elements and prevents a volume of the medium from being disposed therebetween.

18. The device of claim 14 wherein the first and second conductive elements along with the insulating dielectric are flexed so that they are shaped like an arch.

19. The device of claim 14 wherein the insulating dielectric is selected from the group consisting of polyethylene, polystyrene, Teflon, polyester, plastic resins and Mylar.

20. The device of claim 14 wherein the value of the inductor element is selected so that the resonance frequency of the LC oscillator is greater than 27 MHZ.

21. The device of claim 20 wherein the value of the inductor element is selected so that the resonance frequency is around 200 MHZ.

22. The device of claim 20 wherein the output circuit includes a frequency divider.

23. The device of claim 22 wherein the output signal has a frequency of about 3 MHZ.

24. The device of claim 14 wherein the output circuit is coupled to an output transmission line.

25. The device of claim 24 wherein the transmission line is coupled to a computer, the transmission line delivering the output signal to the computer.

26. The device of claim 14 wherein the insulating dielectric material maintains the first and second conductors in an equidistant relationship relative to one another.

27. The device of claim 26 wherein the insulating dielectric material maintains the first and second conductors in a generally parallel relationship to one another.

28. The device of claim 14 wherein the output circuit includes a voltage controlled oscillator which generates a first output signal having a frequency equal to the resonance frequency.

29. A device for sensing permittivity changes in a sample of a medium, the device comprising:

an LC oscillator circuit having an inductance element and a capacitance element, the inductance element having a relatively constant value L, and the capacitance element having a variable value, C, wherein the value of the capacitance element is dependent upon the permittivity of the sample in which the capacitance element is disposed, the LC oscillator circuit having a resonance frequency dependent upon the the value of the inductance element and the value of the capacitance element given by $1/(2\pi(LC)^{1/2})$, wherein the capacitance element includes first and second conductive elements substantially surrounded by an insulating dielectric material, the inductance element having a first lead and a second lead, the first conductive element being electrically coupled to the first lead of the inductance element and the second conductive element being electrically coupled to the second lead of the inductance element; and, an output circuit coupled to the LC oscillator adapted to output a signal representative of the permittivity of the sample based upon the resonance frequency of the LC oscillator circuit, wherein changes in the output signal are indicative of changes in the permittivity of the sample.

30. The device of claim 29 wherein the output signal is transmitted to a computer.

31. The device of claim 29 wherein the output circuit includes a voltage controlled oscillator which generates a first output signal having a frequency equal to the resonance frequency.

32. A device for sensing permittivity changes in a sample of a medium, the device comprising:

an LC oscillator circuit having an inductance element and a capacitance element, the inductance element having a relatively constant value, L, and the capacitance element having a variable value, C, wherein the value of the capacitance element is dependent upon the permittivity of the sample in which the capacitance element is disposed, the LC oscillator circuit having a resonance frequency dependent upon the value of the inductance element and the value of the capacitance element given by $1/(2\pi(LC)^{1/2})$, wherein the capacitance element includes first and second conductive elements which are separated by an insulating dielectric material along substantially their entire length, the inductance element having a first lead and a second lead, the first conductive element being electrically coupled to the first lead of the inductance element and the second conductive element being electrically coupled to the second lead of the inductance element; and, an output circuit coupled to the LC oscillator adapted to output a signal representative of the permittivity of the sample based upon the resonance frequency of the LC oscillator circuit, wherein changes in the output signal are indicative of changes in the permittivity of the sample.

33. The device of claim 32 wherein the output circuit includes a voltage controlled oscillator which generates a first output signal having a frequency equal to the resonance frequency.

34. The device of claim 33 wherein the first and second conductive elements along with the insulating dielectric are flexed so that they are shaped like an arch.

35. The device of claim 33 wherein the insulating dielectric is selected from the group consisting of polyethylene, polystyrene, Teflon, polyester, plastic resins and Mylar.

36. The device of claim 33 wherein the value of the inductor element is selected so that the resonance frequency of the LC oscillator is greater than 27 MHZ.

37. The device of claim 36 wherein the value of the inductor element is selected so that the resonance frequency is around 200 MHZ.

38. The device of claim 36 wherein the output circuit includes a frequency divider.

39. The device of claim 38 wherein the output signal has a frequency of about 3 MHZ.

40. The device of claim 33 wherein the output circuit is coupled to an output transmission line.

41. The device of claim 40 wherein the transmission line is coupled to a computer, the transmission line delivering the output signal to the computer.

42. The device of claim 33 wherein the insulating dielectric material maintains the first and second conductors in an equidistant relationship relative to one another.

* * * * *